(12) United States Patent
Kodama et al.

(10) Patent No.: US 12,383,755 B2
(45) Date of Patent: Aug. 12, 2025

(54) LIGHT IRRADIATION DEVICE

(71) Applicants: JAPAN LIFELINE CO., LTD., Tokyo (JP); NATIONAL UNIVERSITY CORPORATION HOKKAIDO UNIVERSITY, Hokkaido (JP)

(72) Inventors: Yuki Kodama, Tokyo (JP); Masaki Kuwatani, Hokkaido (JP); Hajime Hirata, Hokkaido (JP); Mikako Ogawa, Hokkaido (JP); Kohei Nakajima, Hokkaido (JP)

(73) Assignees: JAPAN LIFELINE CO., LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 335 days.

(21) Appl. No.: 18/032,678

(22) PCT Filed: Dec. 1, 2020

(86) PCT No.: PCT/JP2020/044595
§ 371 (c)(1),
(2) Date: Apr. 19, 2023

(87) PCT Pub. No.: WO2022/118360
PCT Pub. Date: Jun. 9, 2022

(65) Prior Publication Data
US 2023/0390572 A1     Dec. 7, 2023

(51) Int. Cl.
*A61N 5/06*     (2006.01)

(52) U.S. Cl.
CPC ........... *A61N 5/0603* (2013.01); *A61N 5/062* (2013.01); *A61N 2005/0655* (2013.01)

(58) Field of Classification Search
CPC .................. A61N 5/0603; A61N 5/062; A61N 2005/0655; A61N 2005/0632;
(Continued)

(56) References Cited

U.S. PATENT DOCUMENTS 5,814,039 A     9/1998  Prescott
11,229,808 B2*  1/2022  Barneck .................. A61L 2/085
(Continued)

FOREIGN PATENT DOCUMENTS

CN     110234397 A     9/2019
JP     H08505803 A     6/1996
(Continued)

*Primary Examiner* — Jonathan T Kuo
(74) *Attorney, Agent, or Firm* — MUNCY, GEISSLER, OLDS & LOWE, P.C.

(57) ABSTRACT

A light irradiation device includes a tube including a tube main body and a light emitting portion, a plurality of wiring boards disposed inside the light emitting portion and including a plurality of light emitting elements disposed at an equal interval mounted, an anode lead wire for connecting an anode terminal of each of the wiring boards to a power source, and a cathode lead wire for connecting a cathode terminal of each of the wiring boards to the power source. In the light emitting portion, a central lumen and surrounding lumens that are arrayed at a 90° interval around the central lumen are formed. The wiring boards are disposed in the respective surrounding lumens with the light emitting elements arrayed along a longitudinal direction of the light emitting portion.

15 Claims, 12 Drawing Sheets

(58) Field of Classification Search
CPC ...... A61N 2005/0659; A61N 2005/061; A61N 2005/0651
See application file for complete search history.

(56) References Cited

U.S. PATENT DOCUMENTS

| | | | |
|---|---|---|---|
| 2014/0235942 | A1 | 8/2014 | Hellstrom et al. |
| 2016/0059031 | A1 | 3/2016 | Wescott et al. |
| 2018/0008122 | A1* | 1/2018 | Arai .................. A61B 1/00013 |
| 2018/0035912 | A1 | 2/2018 | Hayman et al. |
| 2019/0217117 | A1* | 7/2019 | Barneck ............ A61M 25/0028 |

FOREIGN PATENT DOCUMENTS

| | | | | |
|---|---|---|---|---|
| JP | 2007511279 | A | | 5/2007 |
| JP | 2016502419 | A | | 1/2016 |
| JP | 2020043897 | A | | 3/2020 |
| WO | WO2006/130365 | A2 | | 12/2006 |
| WO | WO-2019088940 | A2 | * | 5/2019 ............. A61N 5/062 |

* cited by examiner

LIGHT IRRADIATION DEVICE

TECHNICAL FIELD

The present invention relates to a light irradiation device for irradiating an affected area with light having a specific wavelength required for photoimmunotherapy.

BACKGROUND ART

A recent light irradiation device can perform photoimmunotherapy against cancer relatively easily without large-scale equipment, such as a laser oscillator. An introduced example (light-emitting treatment device) of such a light irradiation device includes a tube provided with a light emitting portion having light permeability on a distal end side, a flexible wiring board disposed inside the light emitting portion in the tube and including a light emitting element that emits light having a specific wavelength mounted, a main body portion that is connected to a proximal end portion of the tube and includes a power source for supplying power to the light emitting element, and a lead wire that is inserted in the tube has one end connected to an electrode of the flexible wiring board and the other end connected to the power source (see Patent Document 1 below).

In performing photoimmunotherapy against bile duct cancer with such a light irradiation device, first, an endoscope (side-viewing endoscope) is inserted through a mouth of a patient until a distal end portion of the endoscope reaches the duodenal papilla. Then, the tube is inserted into a bile duct along a guide wire inserted into the bile duct in advance, and the light emitting portion is disposed in contact with or close to the bile duct cancer. Next, the guide wire and the endoscope are removed, leaving only the tube in the body. Then, a proximal end portion of the tube extending from the mouth is extended from the nostril via the nasal cavity.

CITATION LIST

Patent Literature

Patent Document 1: JP 2020-43897 A

SUMMARY OF INVENTION

Technical Problem

For the photoimmunotherapy against bile duct cancer, the entirety of the bile duct cancer developed on the inner wall of the bile duct is preferably irradiated with light uniformly.

Unfortunately, the known light irradiation device has variation in the amount of light emitted (the amount of light irradiation to the cancer) from the light emitting portion.

For example, Patent Document 1 above discloses a light irradiation device in which the flexible wiring board is disposed inside the light emitting portion in the tube. The flexible wiring board is formed in a shape bent at a bent portion with a pair of side portions oppositely disposed and includes a plurality of light emitting elements mounted on each of the side portions. Unfortunately, such a light irradiation device causes variation in the amount of emitted light in a circumferential direction of the light emitting portion.

Patent Document 1 also discloses a light irradiation device in which the flexible wiring board is disposed inside the light emitting portion in the tube. The flexible wiring board is formed twisted into a spiral shape and includes a plurality of light emitting elements mounted on its outer surface. Unfortunately, such a light irradiation device causes variation in the amount of emitted light also in a longitudinal direction of the light emitting portion.

The photoimmunotherapy against bile duct cancer requires the light emitting portion of the light irradiation device to be positioned against the bile duct cancer narrowing the bile duct and the bile duct cancer to be irradiated with light for a long period of time (about two weeks).

However, while the bile duct cancer is irradiated with light, the light emitting portion of the light irradiation device may block the bile duct constricted by the bile duct cancer. This may cause bile to be accumulated in the gallbladder, causing the patient to suffer from jaundice.

The present invention has been made in view of the above-described circumstances.

An object of the present invention is to provide a light irradiation device capable of irradiating cancer developed on an inner wall of a body duct with light having a specific wavelength in a circumferential direction of the body duct uniformly without variation in the amount of light emitted from the light emitting portion in the circumferential direction.

Another object of the present invention is to provide a light irradiation device capable of irradiating the entirety of cancer developed on an inner wall of a body duct with light having a specific wavelength uniformly without variation in the amount of emitted light in the circumferential direction and the longitudinal direction of the light emitting portion.

Still another object of the present invention is to provide a light irradiation device enabling emission of a body fluid (drainage) during photoimmunotherapy even when a light emitting portion is disposed so as to block the portion constricted by cancer.

Solution to Problem (1) A light irradiation device according to the present invention is a light irradiation device for irradiating an affected area (cancer) with light having a specific wavelength required for photoimmunotherapy and includes:
- a tube including a tube main body and a light emitting portion that has light permeability and is connected to a distal end side of the tube main body;
- a plurality of wiring boards disposed inside the light emitting portion of the tube and including a light emitting element that emits the light having the specific wavelength mounted;
- an anode lead wire extending inside the tube to connect an anode terminal of each of the wiring boards to a power source; and
- a cathode lead wire extending inside the tube to connect a cathode terminal of each of the wiring boards to the power source.

In the light emitting portion, a central lumen extending along a center axis of the tube and a plurality of surrounding lumens that are arrayed at an equal angular interval around the central lumen (that is, along a circumferential direction of the light emitting portion) and are closed on a distal end side of the light emitting portion are formed, and
- the wiring boards are disposed in the respective surrounding lumens with the light emitting element disposed facing an outer side of the light emitting portion in a radial direction.

According to the light irradiation device with such a configuration, photoimmunotherapy against cancer can be performed by inserting the tube into the body, disposing the light emitting portion in contact with or close to the affected area (cancer) to which the photosensitive substance for the photoimmunotherapy is attached, energizing the plurality of wiring boards through the anode lead wire and the cathode lead wire, causing the light emitting element mounted on each of the wiring boards, and irradiating the photosensitive substance and the like attached to the cancer with light.

The wiring board on which the light emitting element is mounted is disposed in each of the plurality of surrounding lumens arrayed at an equal angular interval around the central lumen of the light emitting portion. This allows light having a specific wavelength to be radially emitted without variation in the circumferential direction of the light emitting portion, enabling uniform light irradiation to the affected area (the photosensitive substance and the like attached to the cancer) around the light emitting portion.

In addition, even when the light emitting portion is disposed to block a constricted portion of a body duct through which body fluid, such as bile, flows, flowing the body fluid through the central lumen of the light emitting portion allows the body fluid to be emitted to the outside of the body. Further, flowing the body fluid through the central lumen causes light from the light emitting element mounted on the wiring board disposed in each of the surrounding lumens not to be blocked by the body fluid.

(2) In the light irradiation device according to the present invention, preferably, each of the wiring boards includes a plurality of the light emitting elements disposed at a substantially equal interval and mounted, and the wiring boards are disposed in the respective surrounding lumens with the plurality of the light emitting elements arrayed along a longitudinal direction of the light emitting portion while facing the outer side of the light emitting portion in the radial direction.

According to the light irradiation device with such a configuration, the wiring board is disposed in each of the plurality of surrounding lumens arrayed at an equal angular interval around the central lumen of the light emitting portion with the light emitting elements arrayed along the longitudinal direction of the light emitting portion. This allows light having a specific wavelength to be radially emitted without variation in the circumferential direction and the longitudinal direction of the light emitting portion, enabling uniform light irradiation to the entirety of the affected area (photosensitive substance and the like attached to the cancer) around the light emitting portion.

(3) In the light irradiation device according to the present invention, preferably, four of the surrounding lumens are formed at a 90° interval around the central lumen.

According to the light irradiation device with such a configuration, the four wiring boards can be arranged along the circumferential direction of the light emitting portion, enabling even and uniform light irradiation to the affected area around the light emitting portion.

(4) In the light irradiation device according to the present invention, preferably, in the tube main body of the tube, a first lumen communicating with the central lumen of the light emitting portion and extending in parallel to the center axis while being displaced in a radial direction of the tube from the center axis of the tube and a second lumen extending in parallel to the first lumen and opening to a proximal end surface of the tube are formed, and the anode lead wire and the cathode lead wire are inserted in the second lumen from each of the surrounding lumens, extend in the second lumen, and extend from an opening in the proximal end surface.

According to the light irradiation device with such a configuration, in the tube main body, the anode lead wire and the cathode lead wire extend in the second lumen, and body fluid of a patient can be flowed through the first lumen. Thus, the body fluid of the patient does not come into contact with the anode lead wire and the cathode lead wire inside the tube main body, and, for example, short circuit between the lead wires and contamination of the lead wires due to the contact with the body fluid can be avoided.

In addition, the first lumen is displaced in the radial direction of the tube from the center axis of the tube. Thus, a cross-sectional area of the second lumen serving as the insertion space for the lead wires can be sufficiently increased, and using the light irradiation device of (7) described below allows the body fluid of the patient flowed through the first lumen to be emitted from a side periphery of the tube main body.

(5) In the light irradiation device according to (4) described above, preferably, the tube includes, between the light emitting portion and the tube main body, a lumen switching portion sealing the anode lead wire and the cathode lead wire and formed with a communication path through which the central lumen and the first lumen communicate with each other.

According to the light irradiation device with such a configuration, the communication path of the lumen switching portion allows the central lumen of the light emitting portion and the first lumen of the tube main body to reliably communicate with each other.

In addition, in the lumen switching portion, the anode lead wire and the cathode lead wire are sealed (fixed by the resin forming the lumen switching portion). This can reliably prevent, in connecting, for example, the proximal end portions of the lead wires to the power source, the lead wires from being pulled in the proximal end direction to cause the distal end portions of the lead wires to be detached from electrode terminals of the wiring board or the lead wires being entangled in the lumen switching portion.

(6) In the light irradiation device according to (4) or (5) described above, preferably, a plurality of the anode lead wires and a plurality of the cathode lead wires inserted in the second lumen are each combined into one lead wire, and each lead wire extends from the opening in the proximal end surface of the tube.

According to the light irradiation device with such a configuration, the anode lead wires and the cathode lead wires are each combined into one lead wire, enabling simple operation of connecting the proximal end portions of these lead wires to the power source.

(7) In the light irradiation device according to (4) to (6) described above, preferably, the first lumen is closed on a proximal end side of the tube, and a side hole extending from an outer periphery of the tube main body to the first lumen is formed in a peripheral wall of the tube main body.

According to the light irradiation device with such a configuration, the body fluid of the patient flowing through the first lumen can be emitted from the opening of the side hole, allowing the anode lead wire and the cathode lead wire extending from the opening in the proximal end surface of the tube to be prevented from coming into contact with the body fluid emitted (using the opening as a liquid emission port).

(8) In the light irradiation device according to (7) described above, preferably, the outer periphery of the tube main body is provided with marking indicating a position of an opening of the side hole, allowing the position of an opening with a small diameter to be easily recognized.

(9) In the light irradiation device according to the present invention, preferably, a lead protection sheath is attached to a proximal end side of the tube, and the lead protection sheath encloses the anode lead wire and the cathode lead wire extending from the opening in the proximal end surface of the tube and is easily detachable from the tube.

According to the light irradiation device with such a configuration, the lead wires (the anode lead wire and the cathode lead wire) extending from the opening in the proximal end surface of the tube can be prevented from being wet with snivel or the like when the proximal end portion of the tube extending from the mouth is extended from the nostril via the nasal cavity. In addition, detaching the lead protection sheath from the tube after extending the proximal end portion of the tube from the nostril of the patient allows the unwet proximal end portions of the lead wires to be connected to the power source.

(10) In the light irradiation device according to the present invention, preferably, the tube includes, on a distal end side of the light emitting portion, a most distal end portion having a single lumen structure formed with a lumen communicating with the central lumen.

According to the light irradiation device with such a configuration, the body fluid on the distal end side of the light emitting portion disposed to block the constricted portion can be flowed through the central lumen of the light emitting portion via the lumen of the most distal end portion and emitted to the outside of the body.

(11) In the light irradiation device according to (10) described above, preferably, a peripheral wall of the most distal end portion includes at least one side hole extending from an outer periphery of the most distal end portion to the lumen.

According to the light irradiation device with such a configuration, even when the body fluid cannot be flowed into the lumen from the opening at the distal end of the most distal end portion due to the opening in contact with the inner wall or the like of the body duct, the body fluid can be flowed into from the side hole.

(12) In the light irradiation device according to (10) or (11) described above, preferably, the lumen of the most distal end portion has a larger diameter than a diameter of the central lumen of the light emitting portion, and the tube includes, between the light emitting portion and the most distal end portion, a lumen diameter expansion portion formed with a diameter expansion communication path through which the central lumen and the lumen of the most distal end portion communicate with each other.

According to the light irradiation device with such a configuration, an amount of inflow of body fluid into the lumen of the most distal end portion and thus an amount of emission of the body fluid can be sufficiently increased.

(13) The light irradiation device according to the present invention can be suitably used for photoimmunotherapy against bile duct cancer or pancreatic cancer.

According to the light irradiation device with such a configuration, bile duct cancer developed on an inner wall of a bile duct or pancreatic cancer developed on an inner wall of a pancreatic duct can be irradiated with light having a specific wavelength uniformly in the circumferential direction of the bile duct and the pancreatic duct. Even when the light emitting portion is disposed to block the portion constricted by the bile duct cancer or the pancreatic cancer, the bile can be emitted.

Advantageous Effects of Invention

The light irradiation device according to the present invention is capable of irradiating a cancer developed on an inner wall of a body duct with light having a specific wavelength in the circumferential direction of the body duct uniformly without variation in the amount of light emitted from the light emitting portion in the circumferential direction.

Each of the wiring boards includes the plurality of light emitting elements disposed at a substantially equal interval and mounted, and the wiring boards are disposed in the respective surrounding lumens with the plurality of light emitting elements arrayed along a longitudinal direction of the light emitting portion while facing the outer side of the light emitting portion in the radial direction. This can irradiate the entirety of the cancer developed on an inner wall of a body duct with light having a specific wavelength uniformly without variation in the amount of emitted light along the circumferential direction and the longitudinal direction of the light emitting portion.

Even when the light emitting portion is disposed to block a constricted portion of the body duct, flowing the body fluid through the central lumen of the light emitting portion enables emission of the body fluid (drainage).

Further, flowing the body fluid through the central lumen causes light from the light emitting element mounted on the wiring boards not to be blocked by the body fluid, nor is the amount of light emitted from the light emitting portion reduced due to the blocking of the body fluid.

DESCRIPTION OF EMBODIMENTS

Embodiments

Figure 1:
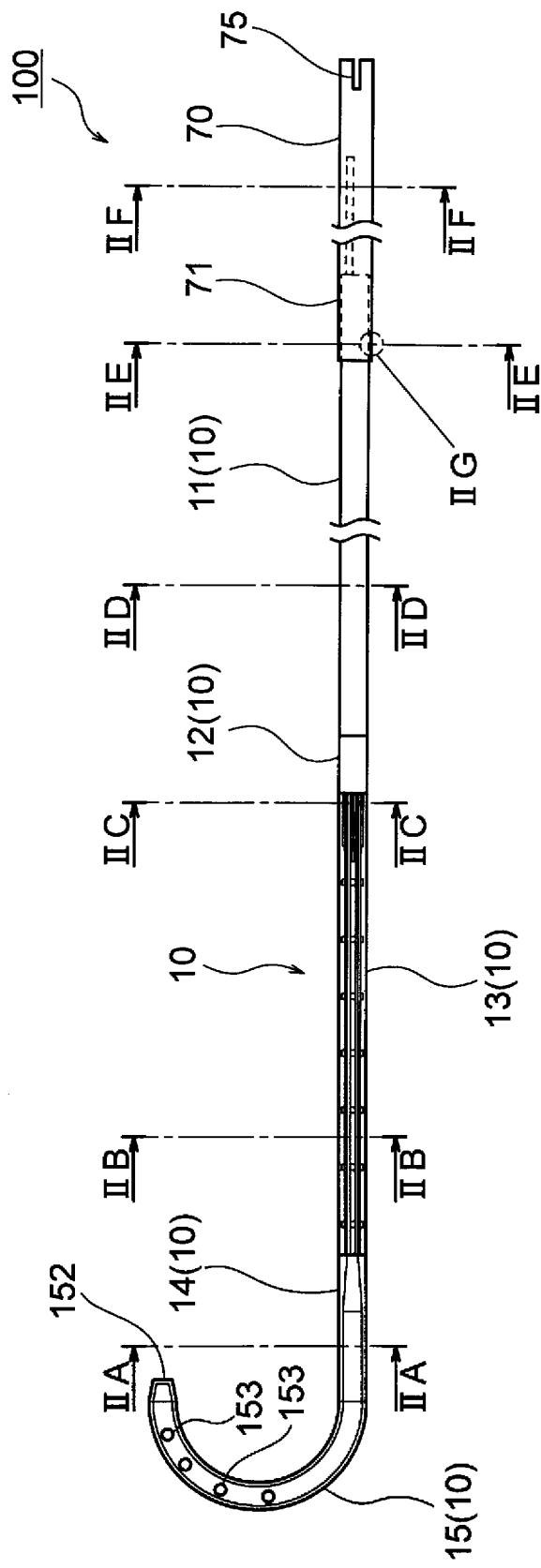
FIG. 1 is a plan view illustrating an embodiment of a light irradiation device according to the present invention.

A light irradiation device 100 of the present embodiment illustrated in FIGS. 1 to 5 is a light irradiation device for irradiating bile duct cancer with near infrared light required for photoimmunotherapy against the bile duct cancer and includes:
- a tube 10 including a tube main body 11, a light emitting portion 13 that has light permeability and is connected to a distal end side of the tube main body 11 via a lumen switching portion 12, and a most distal end portion 15 connected to a distal end side of the light emitting portion 13 via a lumen diameter expansion portion 14;
- four wiring boards 30 disposed inside the light emitting portion 13 of the tube 10 and including seven light emitting elements 35 that emit near infrared light disposed at an equal interval and mounted;
- four anode lead wires 51 extending inside the tube 10 to connect respective anode terminals 36 of the wiring boards 30 to a power source;
- four cathode lead wires 52 extending inside the tube 10 to connect respective cathode terminals 37 of the wiring boards 30 to the power source; and
- a lead protection sheath 70 attached to a proximal end side of the tube 10.

In the light emitting portion 13 of the tube 10, a central lumen 131 extending along a center axis of the tube 10 and surrounding lumens 132 to 135 that are arrayed at a 90° interval around the central lumen 131 and are closed on both end sides of the light emitting portion 13 are formed.

In the tube main body 11 of the tube 10, a first lumen 111 communicating with the central lumen 131 formed in the light emitting portion 13 and extending while being displaced in a radial direction of the tube 10 from the center axis of the tube 10 and a second lumen 112 extending in parallel to the first lumen 111 are formed,
the first lumen 111 is closed on a proximal end side of the tube main body 11, and a side hole 113 extending from an outer periphery of the tube main body 11 to the first lumen 111 is formed in a peripheral wall of the tube main body 11, and
the second lumen 112 is closed on the distal end side of the tube main body 11 and has an opening 114 in a proximal end surface of the tube 10.

In the most distal end portion 15 of the tube 10, a lumen 151 having a larger diameter than a diameter of the central lumen 131 of the light emitting portion 13 and communicating with the central lumen 131 through a diameter expansion communication path 141 of the lumen diameter expansion portion 14 is formed,
the lumen 151 of the most distal end portion 15 has an opening 152 in a distal end surface of the tube 10, and in a peripheral wall of the most distal end portion 15, a plurality of side holes 153 extending from an outer periphery of the most distal end portion 15 to the lumen 151 is formed.

The four wiring boards 30 are disposed in the respective surrounding lumens 132 to 135 with the light emitting elements 35 arrayed along a longitudinal direction of the light emitting portion 13 while facing an outer side of the light emitting portion 13 in a radial direction.

The four anode lead wires 51 pass through the inside of the lumen switching portion 12 from the respective surrounding lumens 132 to 135 of the light emitting portion 13, are inserted in the second lumen 112 of the tube main body 11, extend in the second lumen 112, and are combined into one combined lead wire 51G in the middle of the second lumen 112, and the combined lead wire 51G extends from the tube 10 through the opening 114, and
the four cathode lead wires 52 also pass through the inside of the lumen switching portion 12 from the respective surrounding lumens 132 to 135 of the light emitting portion 13, are inserted in the second lumen 112 of the tube main body 11, extend in the second lumen 112, and are combined into one combined lead wire 52G in the middle of the second lumen 112, and the combined lead wire 52G extends from the tube 10 through the opening 114.

The lead protection sheath 70 is attached to enclose the anode lead wire 51G and the cathode lead wire 52G extending from the opening 114 in the proximal end surface of the tube 10.

The light irradiation device 100 of the present embodiment is used for photoimmunotherapy in which a treatment is performed by bringing the light emitting portion 13 into close contact with bile duct cancer developed on the inner wall of the bile duct and irradiating a photosensitive substance selectively attached to the cancerous tissue with photosensitive light from the light emitting elements 35. Examples of the photosensitive substance can include IR700.

The light irradiation device 100 according to this embodiment includes the tube 10, the four wiring boards 30, the four anode lead wires 51 (one combined lead wire 51G obtained by combining them), the four cathode lead wires 52 (one combined lead wire 52G obtained by combining them), and the lead protection sheath 70.

Figure 5:
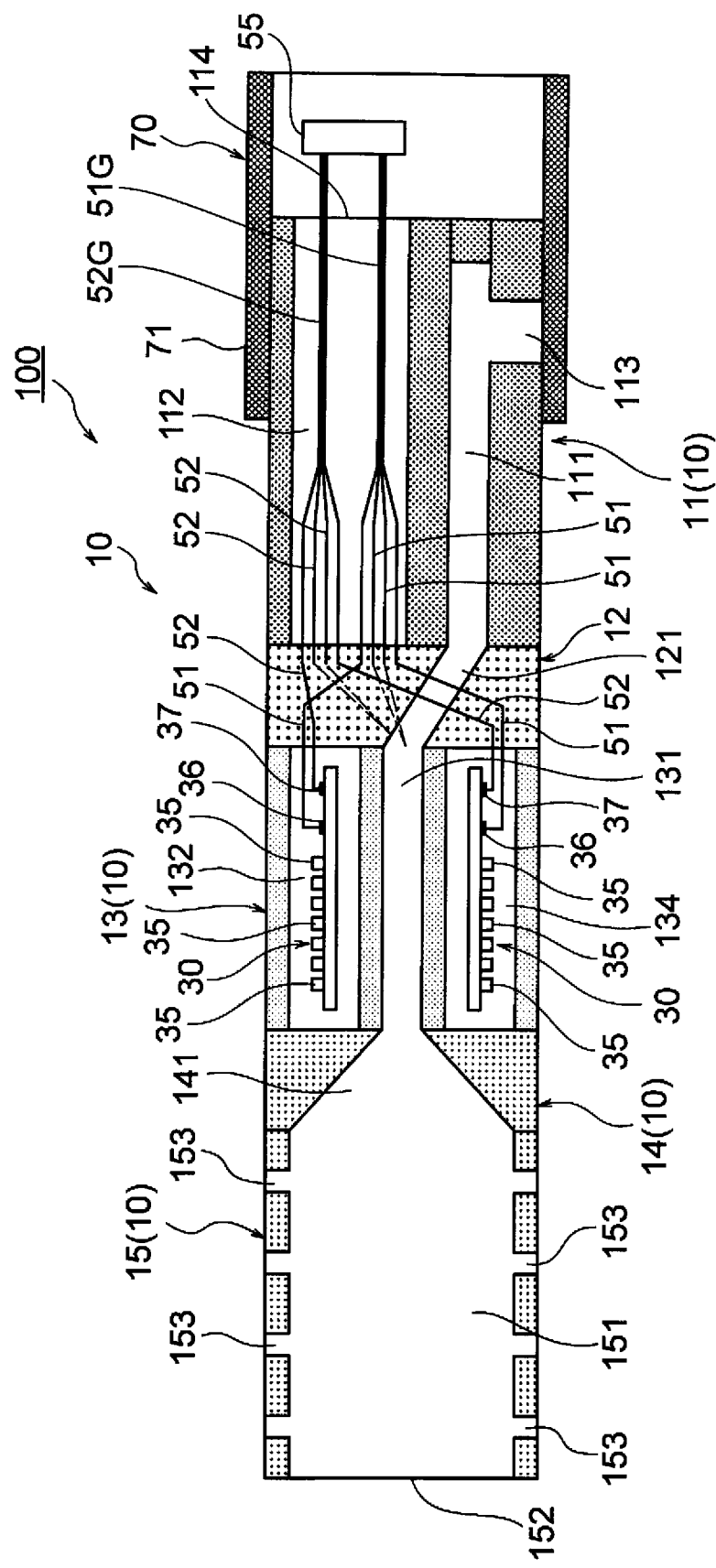
FIG. 5 is a schematic view of the light irradiation device illustrated in FIG. 1.

As illustrated in FIGS. 1 and 5, the tube 10 constituting the light irradiation device 100 includes the tube main body 11, the lumen switching portion 12, the light emitting portion 13, the lumen diameter expansion portion 14, and the most distal end portion 15 in this order from the proximal end side to the distal end side.

The outer diameter of the tube 10 typically ranges from 1.5 to 15 mm and is 2.3 mm as a preferable example.

The length (effective length) of the tube 10 typically ranges from 300 to 5000 mm and is 1500 mm as a preferable example.

The light emitting portion 13 of the tube 10 has light permeability. In the light emitting portion 13, the central lumen 131 and four surrounding lumens 132 to 135 arrayed at a 90° interval along the circumferential direction of the light emitting portion 13 around the central lumen 131 are formed.

As illustrated in FIGS. 2B, 2C, 3 and 4A, the central lumen 131 has a circular cross-section and extends along the center axis of the tube 10.

The central lumen 131 is a bile flowing lumen of the light emitting portion 13 and is open on the distal end side and the proximal end side of the light emitting portion 13.

The diameter of the central lumen 131 typically ranges from 0.1 to 13 mm and is 0.7 mm as a preferable example.

The surrounding lumens 132 to 135 have a rectangular cross section with the four corners rounded (curved). The surrounding lumens 132 to 135 are lumens for accommodating the wiring boards 30, are closed by resin constituting the lumen switching portion 12 on the proximal end side of the light emitting portion 13, and are closed by resin constituting the lumen diameter expansion portion 14 on the distal end side of the light emitting portion 13.

The size (length×width) of the cross section of each of the surrounding lumens 132 to 135 typically ranges from (0.3 mm×0.3 mm) to (3 mm×3 mm) and is (0.6 mm×0.9 mm) as a preferable example.

The length of the light emitting portion 13 typically ranges from 3 to 500 mm and is 40 mm as a preferable example.

The light emitting portion 13 is formed by a material having light permeability. Examples of such a material can include transparent resin materials such as epoxy resin, polycarbonate, acrylic resin, ABS resin, silicone resin, and urethane resin.

The tube main body 11 of the tube 10 is connected to the proximal end side of the light emitting portion 13 via the lumen switching portion 12.

The first lumen 111 and the second lumen 112 are formed in the tube main body 11.

As illustrated in FIGS. 2D, 2E, 3 and 4B, the first lumen 111 has a circular cross-section, is displaced from the center axis of the tube 10 in the radial direction, and extends in parallel to the center axis.

The first lumen 111 is a bile flowing lumen of the tube main body 11, is open on the distal end side of the tube main body 11, and communicates with the central lumen 131 of the light emitting portion 13 through a communication path 121 formed in the lumen switching portion 12.

The diameter of the first lumen 111 typically ranges from 0.4 to 13 mm and is 0.85 mm as a preferable example.

The first lumen 111 is closed on the proximal end side of the tube main body 11, and thus the bile flowing through the first lumen 111 is not emitted from the proximal end surface of the tube 10.

Thus, a side hole 113 extending from the outer periphery of the tube main body 11 to the first lumen 111 is formed in the peripheral wall of the tube main body 11, to serve as an emission path for the bile flowing through the first lumen 111. An opening of the side hole 113 in the outer periphery of the tube main body 11 serves as an emission port for the bile flowing through the first lumen 111.

The shape of the opening of the side hole 113 is, for example, a capsule shape (oval shape), and the size (minor diameter×major diameter) of the opening is 0.8 mm×10 mm as a preferable example.

Preferably, the outer periphery of the tube main body 11 is provided with marking indicating the position of the opening such as painting the edge of the opening, allowing an operator to easily recognize the position of such an opening with a small diameter.

The second lumen 112 has a capsule-shaped (oval-shaped) cross section and is displaced from the center axis of the tube 10 in the radial direction (in a direction opposite to the direction in which the first lumen 111 is displaced) and extends parallel to the center axis and the first lumen 111.

The second lumen 112 is closed by the resin constituting the lumen switching portion 12 on the distal end side of the tube main body 11.

The second lumen 112 is open on the proximal end side of the tube main body 11, and has the opening 114 in the proximal end surface of the tube 10 (tube main body 11).

The second lumen 112 is a lumen through which the lead wires (the anode lead wires 51, the combined lead wire 51G, the cathode lead wires 52, and the combined lead wire 52G) are inserted.

The size (minor diameter×major diameter) of the cross section of the second lumen 112 typically ranges from (0.3 mm×0.3 mm) to (5 mm×5 mm) and is (0.7 mm×1.1 mm) as a preferable example.

The length of the tube main body 11 typically ranges from 500 to 4960 mm and is 1400 mm as a preferable example.

The tube main body 11 is formed by resin. Examples of this resin material can include synthetic resin such as PEBAX, polyurethane, polyamide, polyethylene, and polypropylene.

The lumen switching portion 12 of the tube 10 is interposed between the light emitting portion 13 and the tube main body 11.

In the lumen switching portion 12, the communication path 121 through which the central lumen 131 of the light emitting portion 13 and the first lumen 111 of the tube main body 11 communicate with each other is formed as a flow path for the bile.

The length of the lumen switching portion 12 typically ranges from 1 to 100 mm and is 10 mm as a preferable example.

The lumen switching portion 12 is formed by resin, and the proximal ends of the surrounding lumens 132 to 135 of the light emitting portion 13 and the distal end of the second lumen 112 of the tube main body 11 are closed by the resin constituting the lumen switching portion 12.

Examples of the resin material constituting the lumen switching portion 12 can include the resin constituting the tube main body 11 described above as an example.

The most distal end portion 15 of the tube 10 is connected to the distal end side of the light emitting portion 13 via the lumen diameter expansion portion 14.

The lumen 151 is formed in the most distal end portion 15.

Figure 2A:
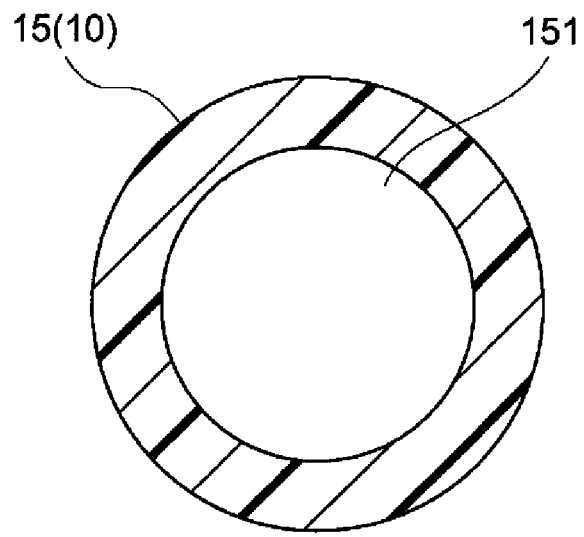
FIG. 2A is an end surface view taken along IIA-IIA in FIG. 1 (an end surface view of a most distal end portion).
Figure 2B:
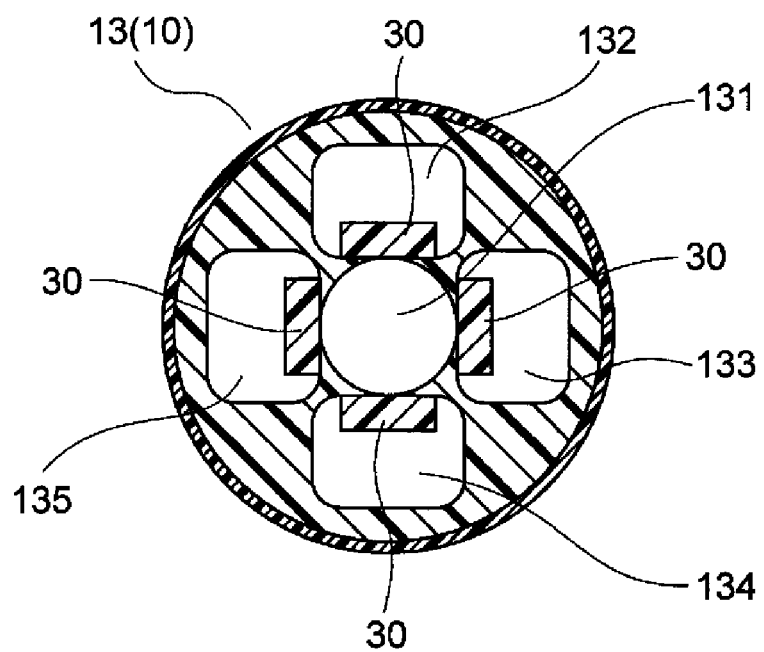
FIG. 2B is an end surface view taken along IIB-IIB in FIG. 1 (an end surface view of a light emitting portion).
Figure 2C:
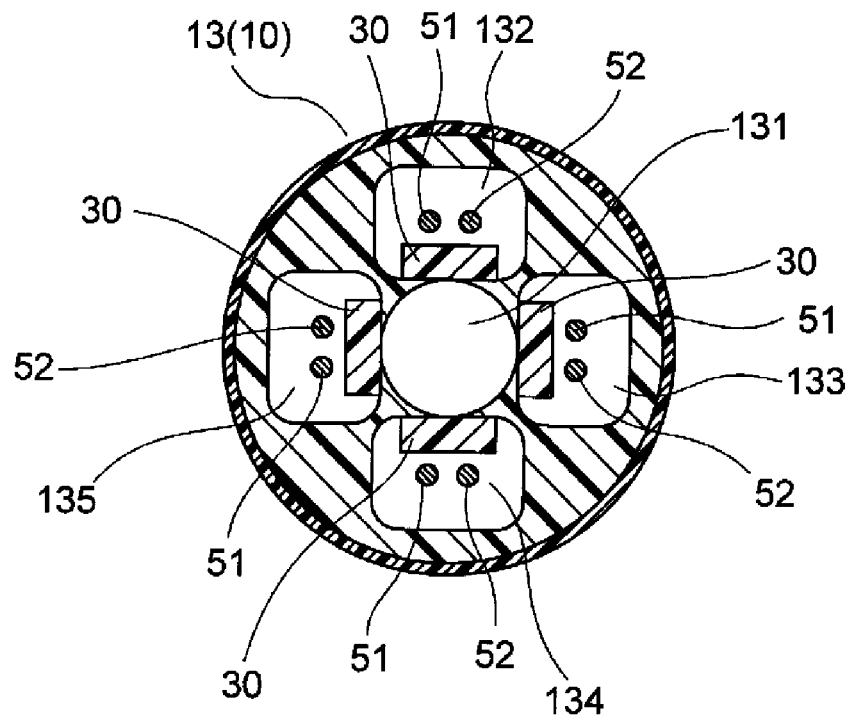
FIG. 2C is an end surface view taken along IIC-IIC in FIG. 1 (an end surface view of the light emitting portion).
Figure 2D:
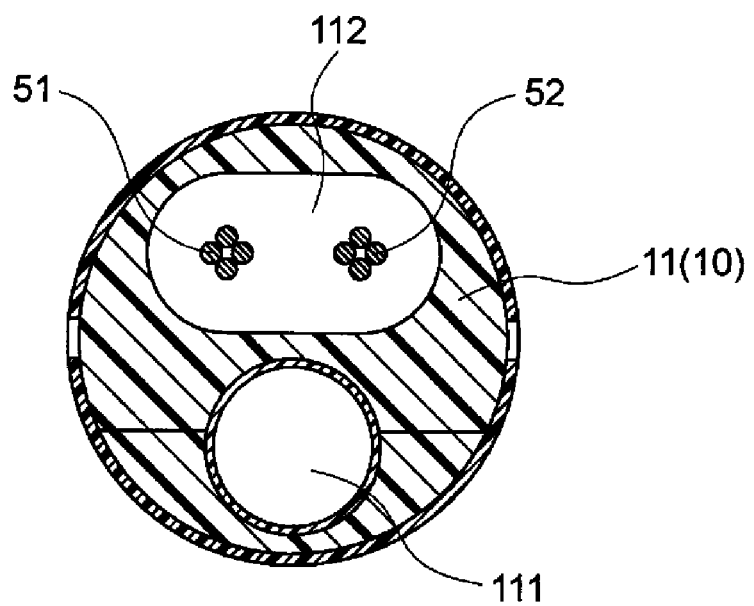
FIG. 2D is an end surface view taken along IID-IID in FIG. 1 (an end surface view of a tube main body).
Figure 2E:
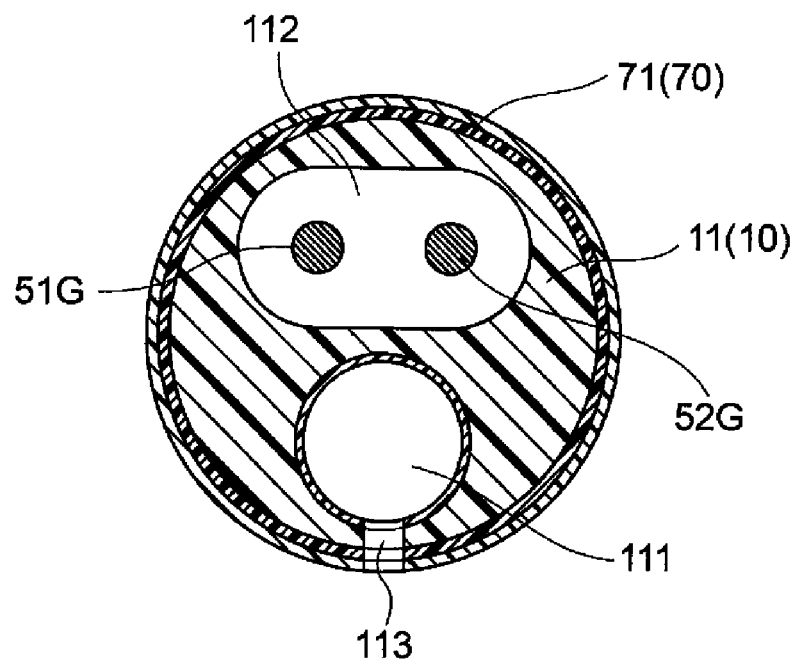
FIG. 2E is an end surface view taken along IIE-IIE in FIG. 1 (an end surface view of the tube main body and a lead protection sheath).
Figure 2F:
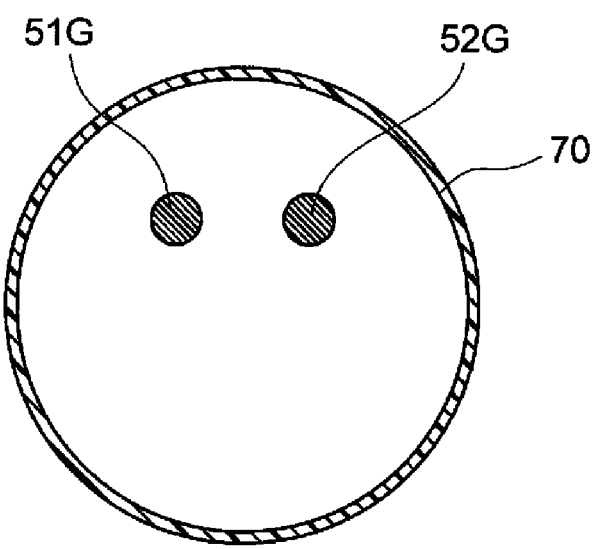
FIG. 2F is an end surface view taken along IIF-IIF in FIG. 1 (an end surface view of the lead protection sheath).
Figure 2G:
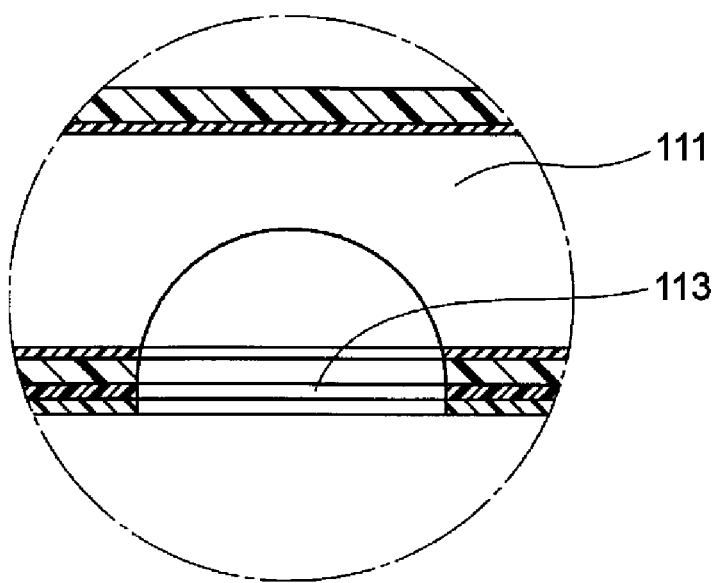
FIG. 2G is a detail view of part IIG in FIG. 1.

As illustrated in FIG. 2A, the lumen 151 has a circular cross section and extends along the center axis of the tube 10.

The lumen 151 is open on the proximal end side of the most distal end portion 15, and communicates with the central lumen 131 of the light emitting portion 13 through the diameter expansion communication path 141 formed in the lumen diameter expansion portion 14.

The lumen 151 is also open on the distal end side of the most distal end portion 15, and has the opening 152 at the distal end of the tube 10.

The plurality of side holes 153 extending from the outer periphery of the most distal end portion 15 to the lumen 151 are formed in the peripheral wall of the most distal end portion 15.

The most distal end portion 15 of the tube 10 is a drainage tube through which the bile accumulated on the distal end side of the light emitting portion 13 flows into the lumen 151 to be emitted to the outside of the body, and the opening 152 and the opening of the side hole 153 serve as inflow ports of the bile.

The diameter the lumen 151 is larger than that of the central lumen 131, typically ranges from 0.5 to 14 mm, and is 1.7 mm as a preferable example.

This can sufficiently increase the amount of inflow of bile into the lumen 151 and thus the amount of emission of the bile.

FIG. 1 illustrates the most distal end portion 15 in a shape curved in J which is its remembered shape. This curved shape can be easily deformed through application of external force (deformed into a linear shape for example), but the curved shape is restored once the external force is released. The most distal end portion 15 of such a curved shape can be latched to the inner wall of the bile duct to dispose the light irradiation device 100 at a predetermined position.

It is a matter of course that the mode for facilitating the latching of the most distal end portion (drainage tube) is not limited to this.

The length of the most distal end portion 15 typically ranges from 10 to 100 mm and is 40 mm as a preferable example.

The lumen diameter expansion portion 14 of the tube 10 is interposed between the light emitting portion 13 and the most distal end portion 15.

In the lumen diameter expansion portion 14, the diameter expansion communication path 141 through which the central lumen 131 of the light emitting portion 13 and the lumen 151 of the most distal end portion 15 communicate with each other is formed as a flow path for the bile.

The diameter expansion communication path 141 is a space of a circular truncated cone shape. The diameter of the diameter expansion communication path 141 at the proximal end of the lumen diameter expansion portion 14 is the same as the diameter of the central lumen 131. The diameter of the diameter expansion communication path 141 at the distal end of the lumen diameter expansion portion 14 is the same as the diameter of the lumen 151.

The length of the diameter expansion communication path 141 typically ranges from 1 to 30 mm and is 10 mm as a preferable example.

The lumen diameter expansion portion 14 is formed by resin, and the distal ends of the surrounding lumens 132 to 135 of the light emitting portion 13 are closed by the resin constituting the lumen diameter expansion portion 14.

Examples of the resin material constituting the lumen diameter expansion portion 14 can include the resin constituting the tube main body 11 described above as an example.

When the light emitting portion 13 is disposed to block the constricted portion of the bile duct, the bile of the patient accumulated around the most distal end portion 15 flows into the lumen 151 from the opening 152 at the distal end of the most distal end portion 15 and the opening of the side hole 153.

The bile that has flowed into the lumen 151 of the most distal end portion 15 flows in the lumen 151, the diameter expansion communication path 141 of the lumen diameter expansion portion 14, the central lumen 131 of the light emitting portion 13, the communication path 121 of the lumen switching portion 12, and the first lumen 111 of the tube main body 11, and is emitted to the outside of the body through the opening (emission port) of the side hole 113 formed in the peripheral wall of the tube main body 11.

As illustrated in FIGS. 2B, 2C, 3, and 4A, the wiring board 30 is disposed in each of the surrounding lumens 132 to 135 of the light emitting portion 13 of the tube 10.

Figure 7A:
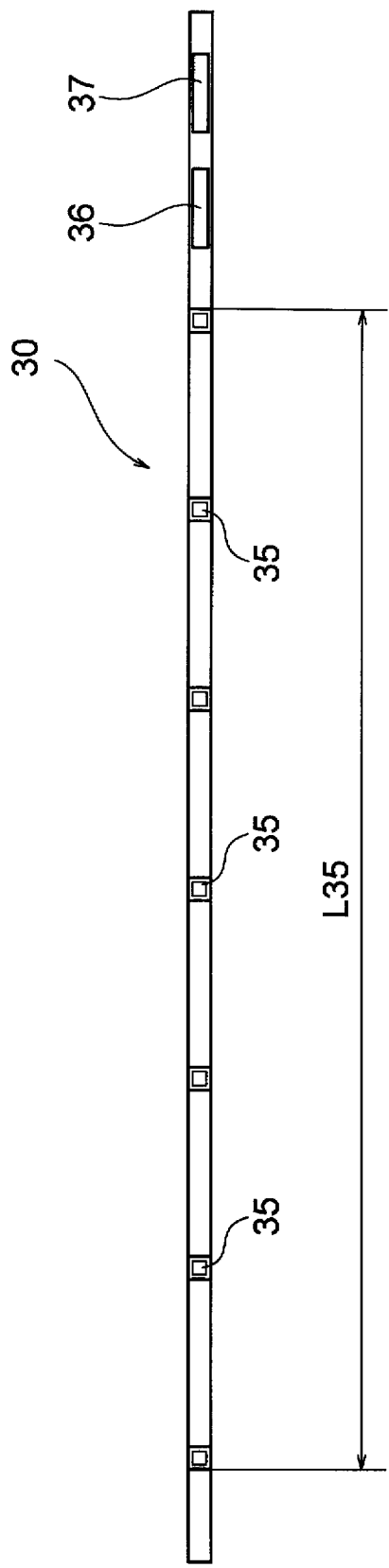
FIG. 7A is a plan view of a wiring board constituting the light irradiation device illustrated in FIG. 1.
Figure 7B:
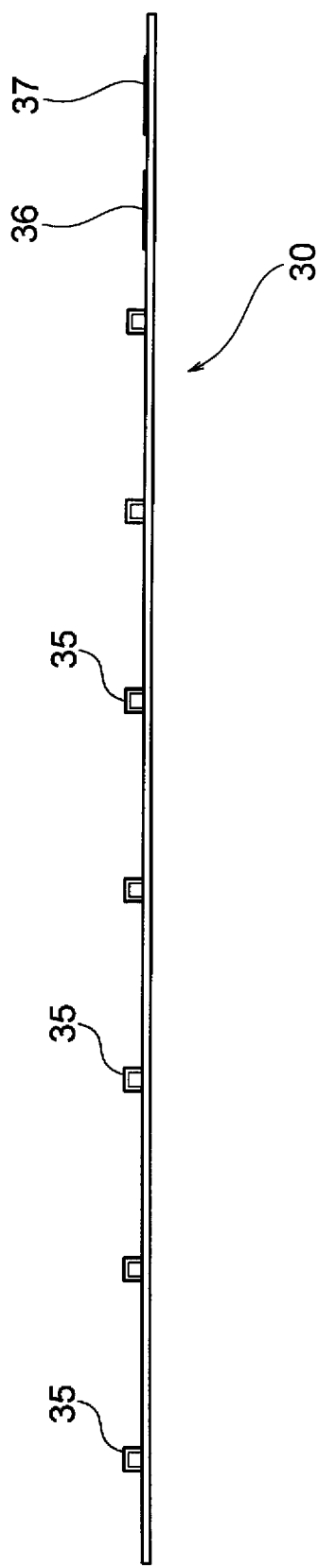
FIG. 7B is a side view of the wiring board constituting the light irradiation device illustrated in FIG. 1.

As illustrated in FIGS. 7A and 7B, the wiring board 30 constituting the light irradiation device 100 has a thin elongated plate shape.

On one surface of the wiring board 30, the seven light emitting elements 35 consisting of LEDs that emit near infrared light (for example, wavelengths of 680 to 700 nm) are disposed at an equal interval along the longitudinal direction of the wiring board 30 and mounted.

The anode terminal 36 and the cathode terminal 37 are disposed on the proximal end side of the wiring board 30.

The length of the wiring board 30 typically ranges from 3 to 450 mm and is 40 mm as a preferable example.

The width of the wiring board 30 typically ranges from 0.3 to 12.5 mm and is 0.55 mm as a preferable example.

The length (L35 in FIG. 7A) of the mounting region of the light emitting elements 35 typically ranges from 5 to 455 mm and is 30 mm as a preferable example.

The wiring board 30 is disposed in each of the surrounding lumens 132 to 135 with the light elements 35 mounted thereon arrayed along the longitudinal direction of the light emitting portion 13 while facing the outer side in the radial direction of the light emitting portion 13.

This causes the four wiring boards 30 to be disposed at a 90° interval along the circumferential direction of the light emitting portion 13. On each of these wiring boards 30, the seven light emitting elements 35 arrayed at an equal interval along the longitudinal direction of the light emitting portion 13, thus the near infrared light from the light emitting elements 35 can be emitted radially in the circumferential direction and the longitudinal direction of the light emitting portion 13 without variation, and the entirety of the bile duct cancer (the photosensitive substance or the like attached thereto) around the light emitting portion 13 can be uniformly irradiated with the near infrared light.

Each of the surrounding lumens 132 to 135 in which the wiring boards 30 are disposed may be filled with a transparent resin material (the resin that is the same as that constituting the light emitting portion for example), to bury the wiring boards 30 in the light emitting portion 13.

This configuration can prevent the displacement of the wiring board 30, light scattering, and the like.

Figure 3:
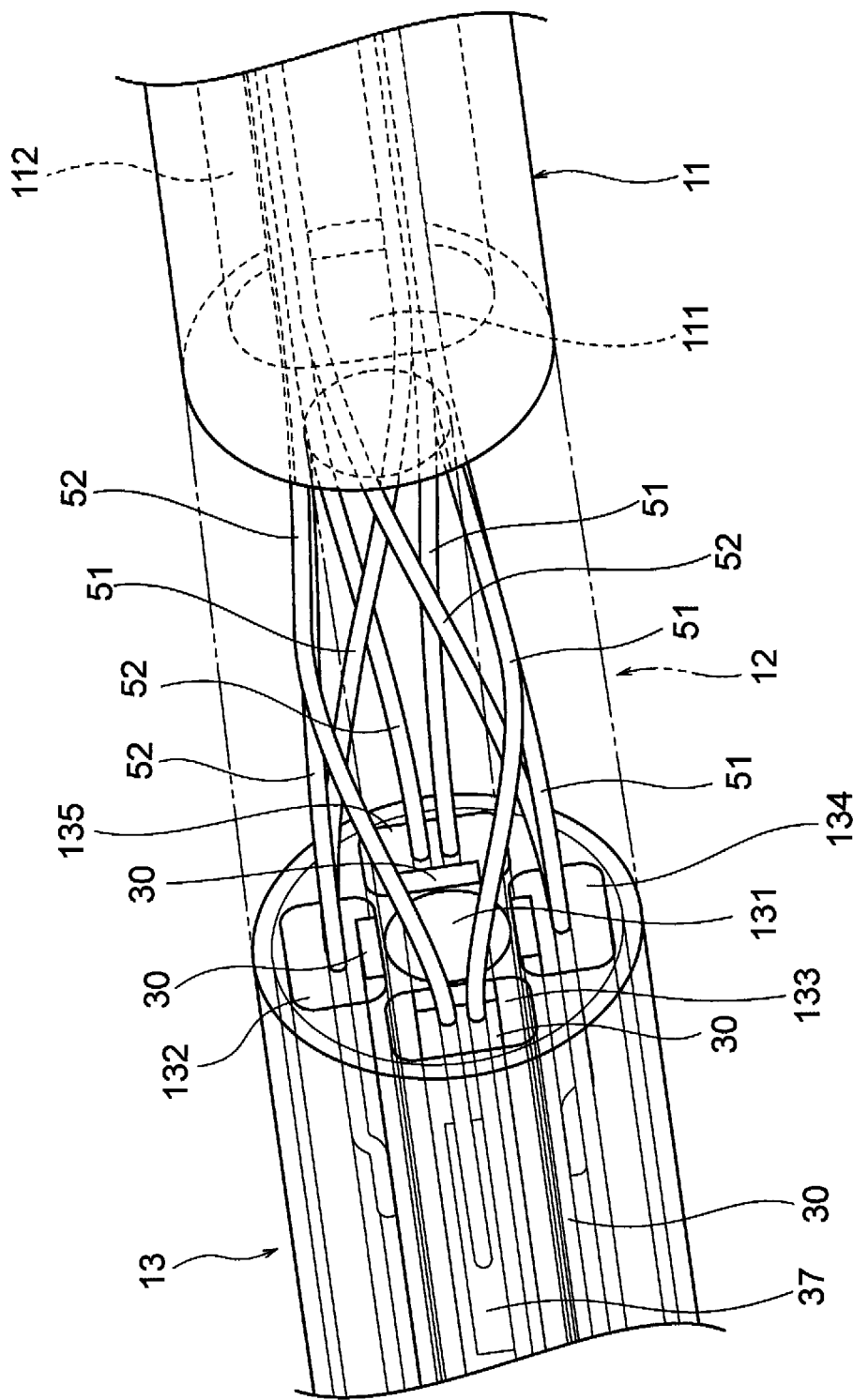
FIG. 3 is a perspective view illustrating a state where lead wires extending from each of surrounding lumens of the light emitting portion are inserted in a second lumen of the tube main body in the light irradiation device illustrated in FIG. 1.
Figure 4A:
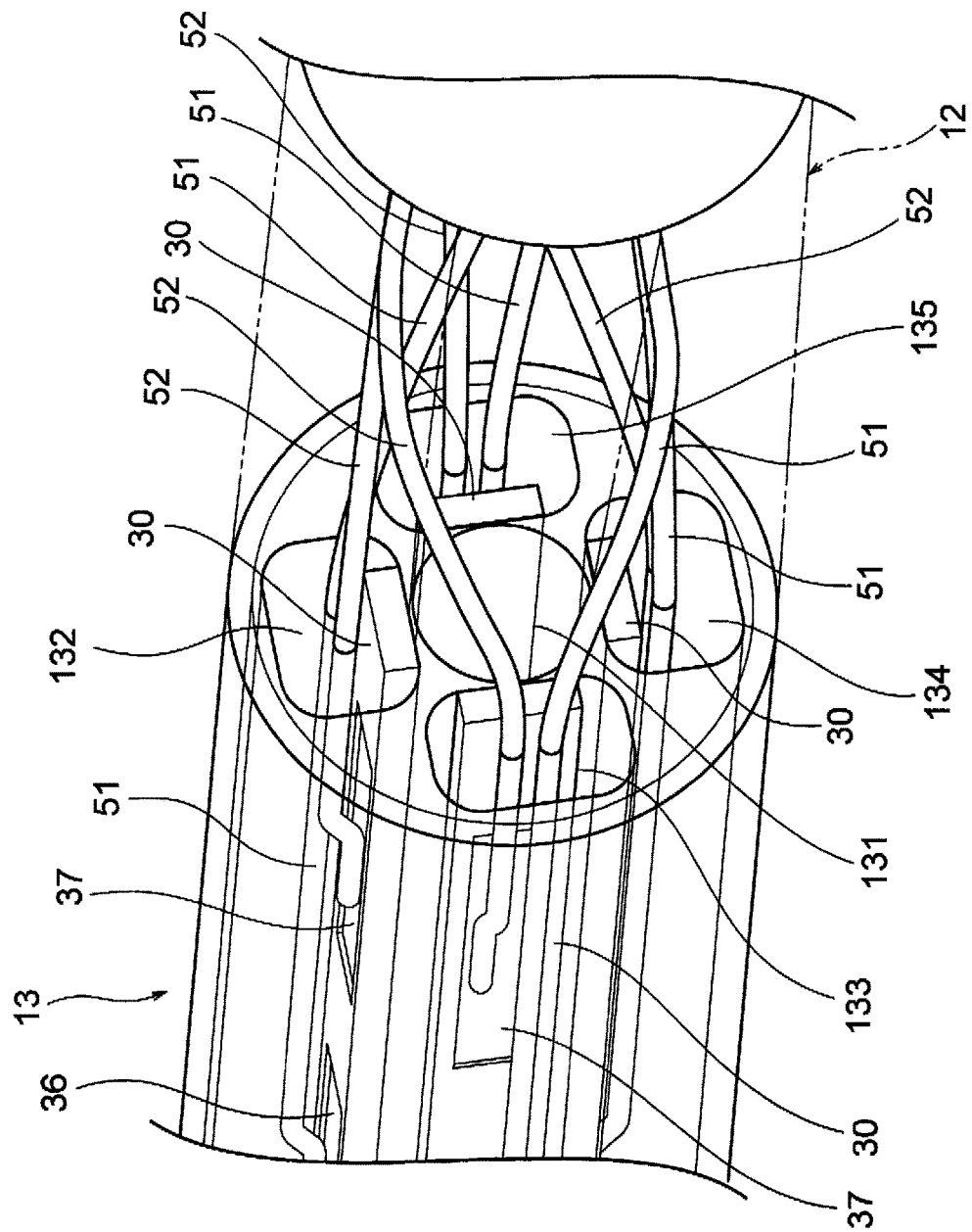
FIG. 4A is a perspective view illustrating the state where lead wires extending from each of surrounding lumens of the light emitting portion are inserted in the second lumen of the tube main body in the light irradiation device illustrated in FIG. 1, as viewed from a proximal end side.
Figure 4B:
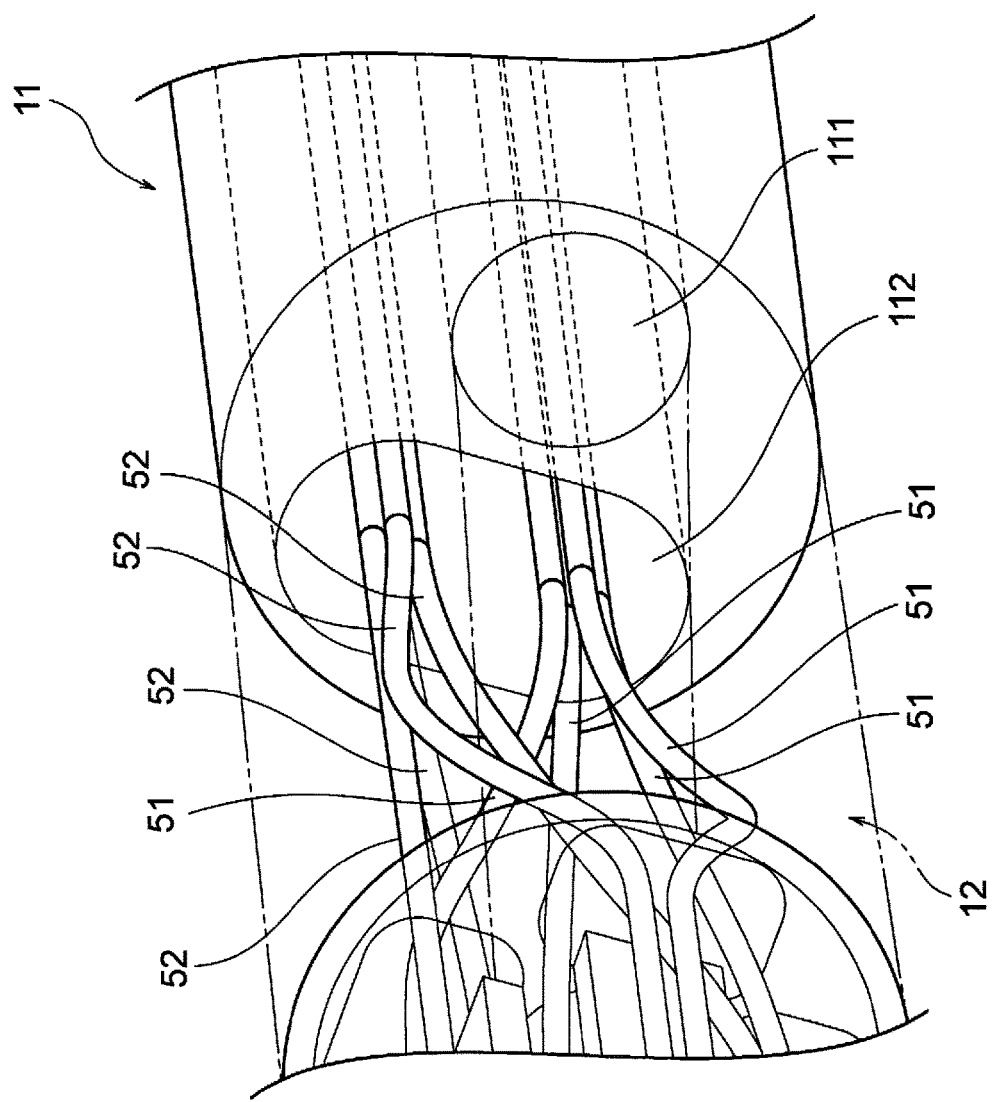
FIG. 4B is a perspective view illustrating the state where lead wires extending from each of surrounding lumens of the light emitting portion are inserted in the second lumen of the tube main body in the light irradiation device illustrated in FIG. 1, as viewed from a distal end side.

As illustrated in FIGS. 3, 4A and 5, the anode terminal 36 and the cathode terminal 37 of the wiring board 30 are respectively connected with the distal end portion of the anode lead wire 51 and the distal end portion of the cathode lead wire 52. Note that FIG. 5 illustrates only two of the four wiring boards 30.

The four anode lead wires 51 of the light irradiation device 100 passes through the inside of the lumen switching portion 12 from the respective surrounding lumens 132 to 135 of the light emitting portion 13 accommodating the wiring boards 30 including the anode terminals 36 to which their distal end portions are connected, to be inserted into the second lumen 112 of the tube main body 11, extend in the second lumen 112, and are combined into the one combined lead wire 51G in the middle of the second lumen 112. The combined lead wire 51G extends from the tube 10 from the opening 114.

Similarly to the anode lead wires 51, the four cathode lead wires 52 of the light irradiation device 100 passes through the inside of the lumen switching portion 12 from the respective surrounding lumens 132 to 135 of the light emitting portion 13 accommodating the wiring boards including the cathode terminals 37 to which their distal end portions are connected, to be inserted into the second lumen 112 of the tube main body 11, extend in the second lumen 112, and are combined into the one combined lead wire 52G in the middle of the second lumen 112. The combined lead wire 52G extends from the tube 10 from the opening 114.

According to the configuration in which the four anode lead wires 51 are combined into the one combined lead wire 51G, the four cathode lead wires 52 are combined into the one combined lead wire 52G, and the combined lead wire 51G and the combined lead wire 52G extend out from the tube 10 as described above, an operation of connecting to the power source only needs to be performed once on each of the anode side and the cathode side and thus can be simplified.

As illustrated in FIGS. 3, 4A, 4B, and 5, the four anode lead wires 51 and the four cathode lead wires 52 are fixed (sealed) in the lumen switching portion 12 by using the resin material constituting the lumen switching portion 12.

Such a configuration can reliably prevent, in connecting the proximal end portion of the combined lead wire 51G or the combined lead wire 52G to the power source, the lead wire from being pulled in the proximal end direction to cause the distal end portion of the anode lead wire 51 or the cathode lead wire 52 to be detached from the anode terminal 36 or the cathode terminal 37 of the wiring board 30 or a plurality of lead wires (the anode lead wires 51 and/or the cathode lead wires 52) from being entangled in the lumen switching portion.

As illustrated in FIG. 5, the proximal end portion of the combined lead wire 51G and the proximal end portion of the combined lead wire 52G are each connected to a device-side connector 55.

Figure 6:
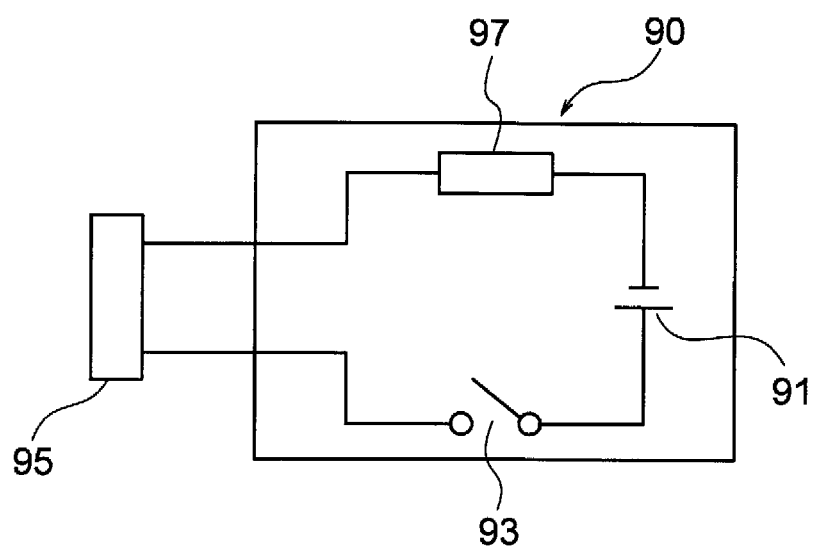
FIG. 6 is a schematic view of a power supply device to which the lead wires of the light irradiation device are connected.

When the device-side connector 55 is connected to a power source-side connector 95 of a power supply device 90 illustrated in FIG. 6, the proximal end portion of the combined lead wire 51G and the proximal end portion of the combined lead wire 52G are each connected to a power source 91 (anode and cathode) of the power supply device 90.

This causes the anode terminal 36 of each of the wiring boards 30 to be electrically connected to the power source 91 (anode) of the power supply device 90 via the anode lead wire 51 (combined lead wire 51G) and the cathode terminal 37 of each of the wiring boards 30 to be electrically connected to the power source 91 (cathode) of the power supply device 90 via the anode lead wire 52 (combined lead wire 52G).

The power source 91 constituting the power supply device 90 is not limited to a particular source and consists of, for example, a button battery.

The power supply device 90 includes an ON-OFF switch 93 for the power source 91 and a variable resistor 97 with which current from the power source 91 varies for the adjustment of the amount of light emitted from the light emitting elements 35.

As illustrated in FIGS. 1, 2E, 2F, and 5, the lead protection sheath 70 is attached to the proximal end side of the tube 10.

The lead protection sheath 70 of the light irradiation device 100 is attached to completely enclose the combined lead wire 51G and the combined lead wire 52G extending from the opening 114 in the proximal end surface of the tube 10.

The lead protection sheath 70 consists of a peel-away sheath having a proximal end portion provided with a cut 75, and can be torn from the cut 75 to be easily removable from the tube 10.

The length of the lead protection sheath 70 typically ranges from 10 to 3000 mm and is 1100 mm as a preferable example.

In this embodiment, the lead protection sheath 70 is attached to the proximal end side of the tube 10, with a distal end portion 71 of the lead protection sheath 70 overlapped with and tentatively bonded to the proximal end portion of the tube 10 (for example, 60 to 100 mm from the proximal end and 80 mm from the proximal end) as a preferable example.

Photoimmunotherapy against bile duct cancer can be performed by using the light irradiation device 100 of the present embodiment as in (1) to (8) below.
(1) Conjugates of antibodies and photosensitive substances (for example, IR700) are administered into the body by intravenous injection or the like, and the conjugates are attached to the cancerous tissue of the bile duct cancer.
(2) The tube 10 of the light irradiation device 100 is inserted into a working lumen of an endoscope (side-viewing endoscope).
(3) The endoscope is inserted into the mouth of the patient until the distal end portion of the endoscope reaches the duodenal papilla.
(4) A guide wire inserted through the inside of the tube 10 (the first lumen 111, the communication path 121, the central lumen 131, the diameter expansion communication path 141, and the lumen 151) is inserted into the bile duct.
(5) The tube 10 is inserted into the bile duct along the guide wire, and the light emitting portion 30 is disposed in contact with the bile duct cancer (that is, so as to block the portion constricted by the bile duct cancer with the light emitting portion 30).
(6) The guide wire and the endoscope are removed, leaving only the tube 10 in the body.
(7) The proximal end portion of the tube 10 extending from the mouth is extended from the nostril via the nasal cavity.
(8) A switch 93 of the power supply device 90 is turned on to supply power from the power source 91 to the light emitting elements 35 of the wiring boards 30, to make the light emitting elements 35 emit light with which the bile duct cancer around the light emitting portion 13 is irradiated. This can perform the photo-immunotherapy through reaction of the photosensitive substance attached to the cancerous tissue.

In the light irradiation device 100 of this embodiment, the wiring boards 30 each having the seven light emitting elements 35 arrayed at an equal interval along the longitudinal direction of the light emitting portion 13 are disposed in the four respective surrounding lumens 132 to 135 arrayed at a 90° interval around the central lumen 131 of the light emitting portion 13. Thus, the near infrared light can be radially emitted without variation in the circumferential direction and the longitudinal direction of the light emitting portion 13, enabling uniform light irradiation to the entirety of bile duct cancer around the light emitting portion 13.

Even when the light emitting portion 13 is arranged to block the constricted portion of the bile duct, the bile can be flowed into the lumen 151 of the most distal end portion 15 serving as the drainage tube and flowed through the diameter expansion communication path 141 of the lumen diameter expansion portion 14, the central lumen 131 of the light emitting portion 13, the communication path 121 of the lumen switching portion 12, and the first lumen 111 of the tube main body 11, and emitted to the outside of the body through the opening of the side hole 113 formed in the peripheral wall of the tube main body 11.

The bile flowing through the central lumen 13 does not block the near infrared light emitted from the light emitting elements 35 mounted on the wiring boards 30 disposed in the respective surrounding lumens 132 to 135.

In the tube main body 11, the anode lead wires 51 (combined lead wire 51G) and the cathode lead wires 52 (combined lead wire 52G) extend in the second lumen 112, and the bile of the patient can be flowed through the first lumen 111. Thus, the bile of the patient does not come into contact with these lead wires, and, for example, short circuit between the anode lead wires 51 and the cathode lead wires 52 and contamination of the lead wires due to the contact with the bile can be avoided.

The combined lead wire 51G and the combined lead wire 52G extend from the opening 114 of the second lumen 112 in the proximal end surface of the tube 10 and the bile flowing through the first lumen 111 can be emitted to the outside of the body through the side hole 113 formed in the peripheral wall of the tube main body 11. Thus, the combined lead wire 51G and the combined lead wire 52G extending from the opening 114 can be prevented from coming into contact with the bile.

The anode lead wires 51 and the cathode lead wires 52 sealed (fixed) in the lumen switching portion 12 by using the resin material constituting the lumen switching portion 12. This can reliably prevent, in connecting the proximal end portion of the combined lead wire 51G or the combined lead wire 52G to the power source, the lead wire from being pulled in the proximal end direction to cause the distal end portion of the anode lead wire 51 or the cathode lead wire 52 to be detached from the anode terminal 36 or the cathode terminal 37 of the wiring board 30 or a plurality of lead wires (the anode lead wires 51 and/or the cathode lead wires 52) from being entangled in the lumen switching portion.

According to the four anode lead wires 51 combined into the one combined lead wire 51G and the four cathode lead wires 52 combined into the one combined lead wire 52G in the second lumen 112 of the tube main body 11 and with the combined lead wire 51G and the combined lead wire 52G extending out from the tube 10, an operation of connecting to the power source only needs to be performed once on each of the anode side and the cathode side and thus can be simplified.

The lead protection sheath 70 consisting of a peel-away sheath is attached to the proximal end side of the tube main body 11 to enclose the combined lead wire 51G and the combined lead wire 52G extending from the opening 114 of the second lumen 112. Thus, when the proximal end portion of the tube 10 passes through the nasal cavity of the patient to extend from the nostril, the combined lead wires 51G and 52G can be prevented from being wet with snivel of the like. Detaching the lead protection sheath 70 after extending the proximal end portion of the tube 10 from the nostril of the patient allows the unwet combined lead wires 51G and 52G to be connected to the power source.

While an embodiment according to the present invention is described above, the present invention is not limited to this, and modifications can be made as appropriate.

For example, the number of surrounding lumens in which the wiring boards are disposed in the light emitting portion is not limited to four, and may be three to six.

Still, if the number of wiring boards is less than four (meaning that the arranged angle interval exceeds 90°), there may be a region, in the circumferential direction of the light emitting portion, where the amount of emitted light is insufficient. In view of this, the number of wiring boards is preferably four to six, and is most preferably four.

The cancer to be treated with photoimmunotherapy using the light irradiation device according to the present invention is not limited to bile duct cancer, and the treatment can be applied to pancreatic cancer, lung cancer, esophageal cancer, colon cancer, stomach cancer, bladder cancer, prostate cancer, and the like.

REFERENCE SIGNS LIST

100 Light irradiation device
10 Tube
11 Tube main body
111 First lumen
112 Second lumen
113 Side hole
114 Opening (proximal end of tube)
12 Lumen switching portion
121 Communication path
13 Light emitting portion
131 Central lumen
132 to 135 Surrounding lumen
14 Lumen diameter expansion portion
141 Diameter expansion communication path
15 Most distal end portion
151 Lumen at most distal end portion
152 Opening (distal end of tube)
153 Side hole
30 Wiring board
35 Light emitting element
36 Anode terminal
37 Cathode terminal
51 Anode lead wire
51G Combined lead wire
52 Cathode lead wire
52G Combined lead wire
55 Device-side connector
70 Lead protection sheath
71 Distal end portion of lead protection sheath
75 Cut
90 Power supply device
91 Power source
93 ON-OFF switch
95 Power source-side connector
97 Variable resistor

The invention claimed is:

1. A light irradiation device comprising:
a tube including a light emitting portion and inserted into a body,
wherein
the light emitting portion includes a central lumen extending along a center axis of the tube, at least one surrounding lumen arranged around the central lumen, and at least one light emitting element disposed inside the at least one surrounding lumen, the central lumen is open on a distal end side of the tube, and
the at least one surrounding lumen is closed on the distal end side of the tube.

2. The light irradiation device according to claim 1, wherein
the light emitting portion includes a plurality of the surrounding lumens, and
in a cross-sectional view perpendicular to a central axis, the plurality of the surrounding lumens is arrayed along a circumferential direction of the central lumen.

3. The light irradiation device according to claim 2, wherein
the light emitting portion includes four of the plurality of the surrounding lumens, and
in the cross-sectional view perpendicular to the central axis, four of the plurality of the surrounding lumens are arrayed at equal intervals from each other around the central lumen.

4. The light irradiation device according to claim 1, wherein
the at least one surrounding lumen extends along a central axis,
the light emitting portion includes a plurality of the light emitting elements, and
the plurality of the light emitting elements is arrayed along the central axis.

5. The light irradiation device according to claim 1, wherein
the light emitting portion includes a wiring board in the at least one surrounding lumen on which the at least one light emitting element is mounted,
the wiring board includes an anode terminal and a cathode terminal, and
the light irradiation device includes at least one anode lead wire connected to the anode terminal and at least one cathode lead wire connected to the cathode terminal.

6. The light irradiation device according to claim 5, wherein
the tube includes a tube main body on the proximal end side of the tube from the light emitting portion,
the tube main body includes a first lumen communicating with the central lumen and extending in parallel to the center axis, and a second lumen extending along the first lumen and opening on a proximal end side of the tube, and
the at least one anode lead wire and the at least one cathode lead wire are inserted in the second lumen from the at least one surrounding lumen, pass through the second lumen, and extend from an opening of the second lumen.

7. The light irradiation device according to claim 6, wherein
the tube includes, between the light emitting portion and the tube main body, a lumen switching portion, and
the lumen switching portion seal the at least one anode lead wire and the at least one cathode lead wire and includes a communication path through which the central lumen and the first lumen communicate with each other.

8. The light irradiation device according to claim 6, wherein
the light emitting portion includes a plurality of the surrounding lumens,
the plurality of the surrounding lumens each accommodate the wiring board,
a plurality of the anode lead wires inserted in the second lumen from each of the plurality of the surrounding lumens are combined with each other and extends from the opening of the second lumen, and
a plurality of the cathode lead wires inserted in the second lumen from each of the plurality of the surrounding lumens are combined with each other and extends from the opening of the second lumen.

9. The light irradiation device according to claim 6, wherein
the first lumen is closed on a proximal end surface of the tube main body, and
the tube main body includes a side hole extending from an outer periphery of the tube main body to the first lumen.

10. The light irradiation device according to claim 9, wherein the tube main body includes a mark on the outer periphery indicating a position of the side hole.

11. The light irradiation device according to claim 6, further comprising:
a lead protection sheath enclosing the at least one anode lead wire and the at least one cathode lead wire extending from the opening of the second lumen and detachable from the tube.

12. The light irradiation device according to claim 1, wherein
the tube includes a most distal end portion on a distal end side of the tube from the light emitting portion, and
the most distal end portion includes a lumen communicating with the outside of the tube and the central lumen.

13. The light irradiation device according to claim 12, wherein the most distal end portion includes at least one side hole extending from an outer periphery of the most distal end portion to the lumen.

14. The light irradiation device according to claim 12, wherein
the lumen has a larger diameter than a diameter of the central lumen, and
the tube includes a lumen diameter expansion portion between the light emitting portion and the most distal end portion, and
the lumen diameter expansion portion includes a diameter expansion communication path through which the central lumen and the lumen communicate with each other.

15. The light irradiation device according to claim 1 to be used for photoimmunotherapy against at least one of bile duct cancer or pancreatic cancer.

* * * * *